(12) United States Patent
Lindquist

(10) Patent No.: US 6,533,582 B2
(45) Date of Patent: *Mar. 18, 2003

(54) IN-OFFICE TOOTH WHITENING

(75) Inventor: Sherrill F. Lindquist, Dublin, OH (US)

(73) Assignee: Ultradent Products, Inc., South Jordan, UT (US)

( * ) Notice: Subject to any disclaimer, the term of this patent is extended or adjusted under 35 U.S.C. 154(b) by 140 days.

This patent is subject to a terminal disclaimer.

(21) Appl. No.: 09/842,995

(22) Filed: Apr. 26, 2001

(65) Prior Publication Data

US 2001/0038997 A1 Nov. 8, 2001

Related U.S. Application Data

(63) Continuation-in-part of application No. 09/565,752, filed on May 8, 2000.

(51) Int. Cl.[7] .................................................. A61C 5/00
(52) U.S. Cl. ...................................................... 433/215
(58) Field of Search ............................. 433/34, 48, 74, 433/213, 214, 215, 229

(56) References Cited

U.S. PATENT DOCUMENTS

| | | | |
|---|---|---|---|
| 1,084,017 A | 1/1914 | Lautenburg | |
| 2,110,860 A | 3/1938 | Grempler | 32/17 |
| 2,257,329 A | * 9/1941 | Britt | |
| 3,207,161 A | 9/1965 | Dietz | 128/404 |
| 3,215,139 A | 11/1965 | Dietz | 128/172.1 |
| 4,445,854 A | 5/1984 | Bekey et al. | 433/37 |
| 4,959,013 A | 9/1990 | Reynolds | 433/35 |
| 4,983,381 A | 1/1991 | Zaragoza | 424/53 |
| 5,177,120 A | 1/1993 | Hare et al. | 523/109 |
| 5,211,559 A | 5/1993 | Hart et al. | 433/80 |
| 5,316,473 A | * 5/1994 | Hare | 433/29 |
| 5,421,727 A | 6/1995 | Stevens et al. | 433/224 |
| 5,487,662 A | * 1/1996 | Kipke et al. | 433/37 |
| 5,494,441 A | 2/1996 | Nicholson | 433/215 |
| 5,698,610 A | 12/1997 | Futami et al. | 523/109 |
| 6,102,705 A | * 8/2000 | Darnell | 433/216 |

* cited by examiner

Primary Examiner—Nicholas D. Lucchesi
(74) Attorney, Agent, or Firm—Workman, Nydegger, Seeley

(57) ABSTRACT

A dental office procedure for whitening patient teeth involves the basic steps of: (1) coating a specially-prepared patient dentition impression with a tooth whitening agent; (2) placing the coated patient dentition impression into the patient's mouth; (3) heating a specially-prepared patient dentition impression to a temperature in the range of approximately from 120° F. to 140° F. and (4) retaining the so-placed patient dentition impression in position at least for a total period of time in the range of approximately from 5 to 60 minutes. The procedure can be adapted to microwave heating, electrical resistance heating, or hot fluid heating of the patient dentition impression.

17 Claims, 8 Drawing Sheets

IN-OFFICE TOOTH WHITENING

RELATED APPLICATION

This application is a continuation-in-part of copending U.S. application Ser. No. 09/565,752, filed May 8, 2000. For purposes of disclosure, the foregoing application is incorporated herein by specific reference.

BACKGROUND OF THE INVENTION

1. Field of the Invention

This invention relates generally to patient dentition stain removal, and particularly concerns methods, materials, and apparatus which may be advantageously utilized in connection with the whitening or bleaching of a patient's teeth in a dental office.

2. Review of the Relevant Technology

Present conventional dental practice in the United States for effectively changing the inherent color of patient's teeth basically involves: (1) an in-office teeth whitening procedure that generally requires about one-hour of office time, or (2) in-office preparation of a patient kit with instructions, followed by patient use of the kit in teeth whitening treatments at home of from 1 to 8 hours per day repeated for 2 to 6 weeks.

The in-office teeth whitening procedure usually involves, with a protective rubber dam in place in the patient's mouth: (1) protectively coating the patient's gingival tissues; (2) applying to and activating on the teeth to be whitened a hydrogen peroxide or carbamide peroxide gel; and (3) afterwards completing a thorough mouth rinse and removal of the protective coating and rubber dam.

The dentist-prepared kit for patient home-use typically includes a custom-configured patient bleaching tray or mouth-guard formed by a multi-step in-office procedure, a supply of whitening agent such as carbamide peroxide gel, and appropriate instructions for kit home-use by the patient. The typical multi-step dental office procedure utilized for forming the custom patient tooth-whitening mouth-guard or tray for home use is a time-consuming procedure, and typically involves the basic steps of: (1) making conventional alginate impressions of the patient's maxillary and/or mandibular teeth, (2) casting dentition models using state-of-the-art dental laboratory stone casting material and the alginate impressions, followed by trimming-away of un-needed model material, (3) blocking out on the trimmed cast stone models, using a conventional light-cured or light-activated, acrylic-based resin laboratory block-out gel, those tooth areas to be whitened (often excluding all molar teeth), and (4) vacuum forming a 5-inch by 5-inch sheet of 0.040-inch to 0.080-inch thickness clear plastic resin mouth guard material over each blocked-out and trimmed dental stone model, cooling, removing from model, and suitably trimming above the gingival crest. The whitening mouth guard is then ready for delivery to the patient in the patient home-use whitening kit. As indicated above, home-use of the kit mouth guard and kit-included whitening agent (e.g., carbamide peroxide gel) typically requires 1 to 8-hour bleaching treatments repeated daily over a period that generally is in the range of 2 to 6 weeks depending upon the degree or severity of dentition staining.

I have discovered a novel in-office dental procedure that, when utilized as a replacement for the above-described conventional in-office procedures, obtains equally satisfactory whitening results, realizes a significant reduction of required dentist and patient in-office times, and also effects a substantial reduction in the costs of patient teeth whitening treatments.

SUMMARY AND OBJECTS OF THE INVENTION

The present invention relates to the bleaching of teeth involving the use of conventional or specially adapted dental impression trays in conjunction with a dental impression material, heat and a dental bleaching composition. The impression material provides the ability to form a device that can immediately be used to bleach a patient's teeth, typically within an in-office procedure, using a conventional dental bleaching composition. The impression materials can be heated by, e.g., microwave energy, resistive heating devices, or a heated fluid in order to accelerate the rate at which the bleaching composition bleaches the patient's teeth.

A first embodiment of the method aspect of the present invention involves the following steps: (1) applying a dental impression adhesive to the surface of the principal cavity of a conventional (or specially adapted) alginate dental impression tray; (2) optionally applying a dental wax sheet overlay to the surfaces of the patient's teeth to be whitened; (3) filling the coated principal cavity of the dental impression tray with an unset conventional alginate (or other appropriate) dental impression material; (4) placing the filled dental impression tray into the patient's mouth and holding it in place a sufficient length of time to set the unset alginate dental impression material and thereby form a patient dentition impression; (5) removing the alginate dental impression tray and included set alginate patient dentition impression, together with the optional retained wax overlay material, if used, from the patient's mouth; (6) if used, scraping or otherwise removing the retained wax overlay from the alginate patient dentition impression; (7) heating the alginate dental impression tray and included patient alginate dentition impression using any appropriate method to a temperature of at least about 110° F.; (8) coating the surfaces of the patient dentition impression corresponding to the patient teeth that are to be whitened with a conventional carbamide peroxide or hydrogen peroxide tooth bleaching gel; (9) placing the heated alginate dental impression tray and included alginate patient dentition impression with carbamide peroxide coating into the patient's mouth; (10a) if the alginate material is continuously heated, by e.g., resistive heat, holding the tray in place for a desired time period to effect bleaching, while preferably maintaining the temperature above about 110° F.; (10b) if the alginate materials is temporarily heated by means of microwave energy, repeating the sequence of steps (7) through (10b); and (11) removing the alginate dental impression tray and included alginate patient dentition impression from the patient's mouth and thoroughly rinsing the patient's mouth prior to release of the patient.

In a preferred embodiment, the invention involves electrical resistance heating for heating and maintaining the impression material at the desired temperature. Alternatively, the invention may involve the use of heated fluid to maintain the impression material at the desired temperature. In the case of either electrical or fluid heating, steps (7)–(9) may be performed in any desired order.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention encompasses apparatus and methods for bleaching a patient's teeth, typically in an in-office procedure, including a conventional or specially adapted dental impression tray in conjunction with a heated dental impression material and a dental bleaching composition. The impression material provides the ability to form a device that can immediately be used to bleach a patient's teeth, typically within an in-office procedure, using a conventional dental bleaching composition. The heated impression materials, which are heated, e.g., by means of microwave energy, a resistive heating device, or a heated fluid, accelerates the rate at which the bleaching composition bleaches the patient's teeth. Other optional steps may be performed, as desired, to tailor the bleaching process as desired.

Figure 1:
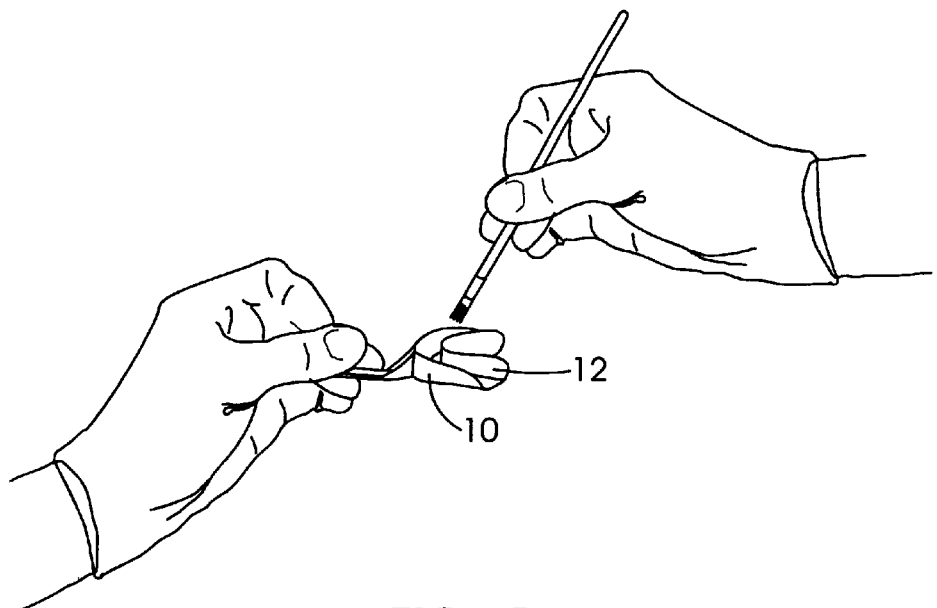
FIG. 1 depicts a preliminary procedural step of coating the principal cavity of an alginate dental impression tray with a conventional adhesive.
Figure 2:
FIG. 2 depicts a preliminary step of applying a dental wax overlay to the surfaces of the patient's teeth that are to be whitened.

As illustrated in FIG. 1, an optional preliminary step to practicing the present invention involves brushing or otherwise applying a dental impression adhesive coating on or to the surface of the principal cavity 12 of a conventional, disposable mandibular alginate dental impression tray 10. In one embodiment, one such tray 10 is required for the mandibular (or lower) teeth that are to be whitened, and a separate but like tray 10 may be used for treating the patient's maxillary (or upper) teeth. It will be appreciated, however, that it is within the scope of the invention to utilize a two-sided impression tray capable of receiving impression material sufficient for both the top and bottom teeth.

As shown in Figure, an additional optional preparatory step is the step of applying a sheet-like conventional dental wax overlay 14 to those surfaces of the patient's teeth that are to be whitened—usually just to the facial aspects of the teeth. The purpose of the wax sheet is to create more space between the formed dental impression and the patient's teeth so as to hold additional bleaching material, if desired.

Figure 3:
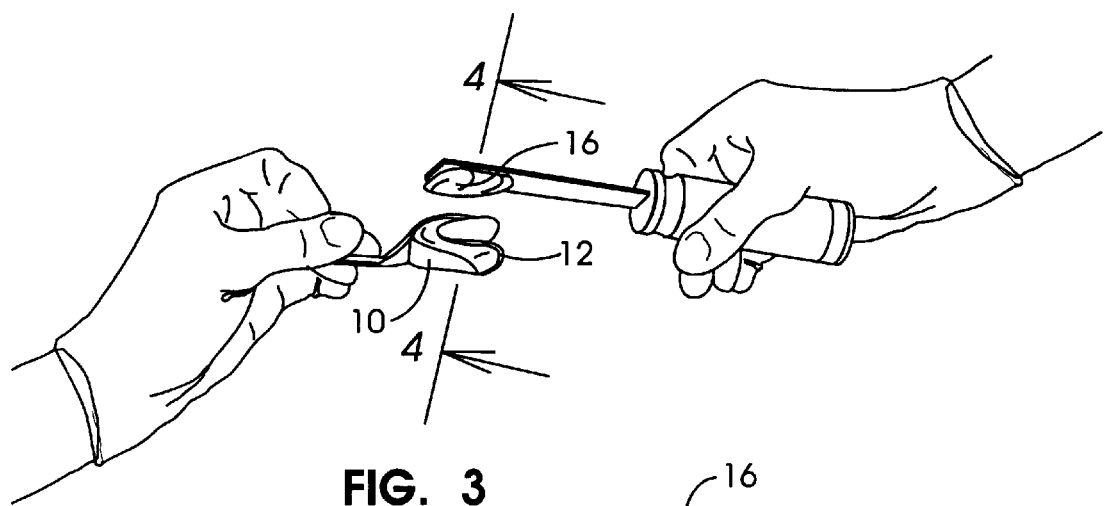
FIG. 3 illustrates the step of placing an unset conventional dental impression material in the principal cavity of the dental impression tray of FIG. 1.
Figure 4:
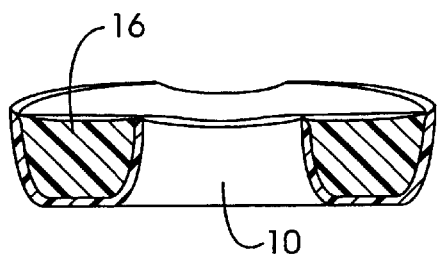
FIG. 4 is a cross-section view taken at line 4—4 of FIG. 3 and extending transversely through the filled dental impression tray of FIG. 3.

Referring to FIG. 3, the next step in the invention method involves filling cavity 12 of impression tray 10 with a suitable quantity of a pre-mixed and unset alginate dental impression material or catalyzed dental impression compound 16. FIG. 4 illustrates the filled dental impression tray in its condition just prior to insertion into the patient's mouth. While alginate impression materials are common and inexpensive, it is certainly within the scope of the invention to use other materials capable of forming and then maintaining an impression of the patient's teeth. Examples of other materials include silicone or polyether, preferably impregnated with fillers or fibers able to impart enhanced heat capacity and/or heat transference properties. Examples include one or more of metals, ceramics or minerals.

Figure 5:
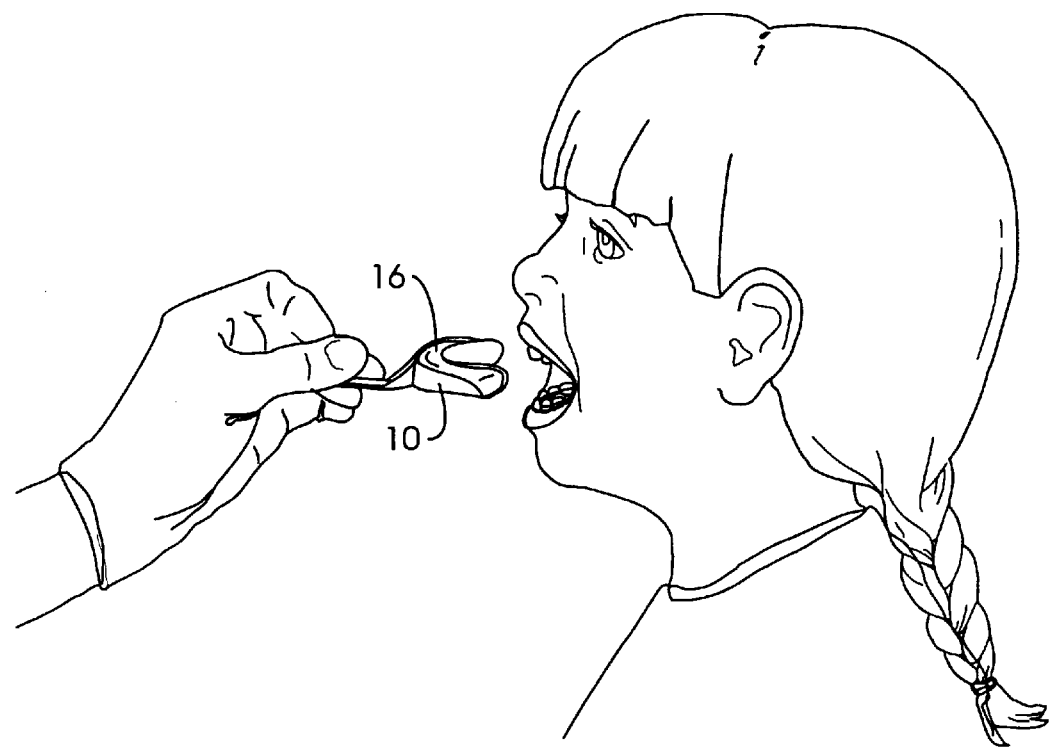
FIG. 5 depicts the act of inserting the compound-filled dental impression tray of FIGS. 3 and 4 into a patient's mouth for impression-setting purposes.

As shown in FIG. 5, the filled dental impression tray is then placed and properly seated in the patient's mouth and held in position for a sufficient length of time for dental impression material 16 to become set. The patient will normally bite down into the unset impression material so as to conform the impression material to the shape of the patient's teeth. The dental impression tray 10 is normally maintained within the patient's mouth until the impression material 16 has at least partially set to yield a cured dental impression 18.

Figure 6:
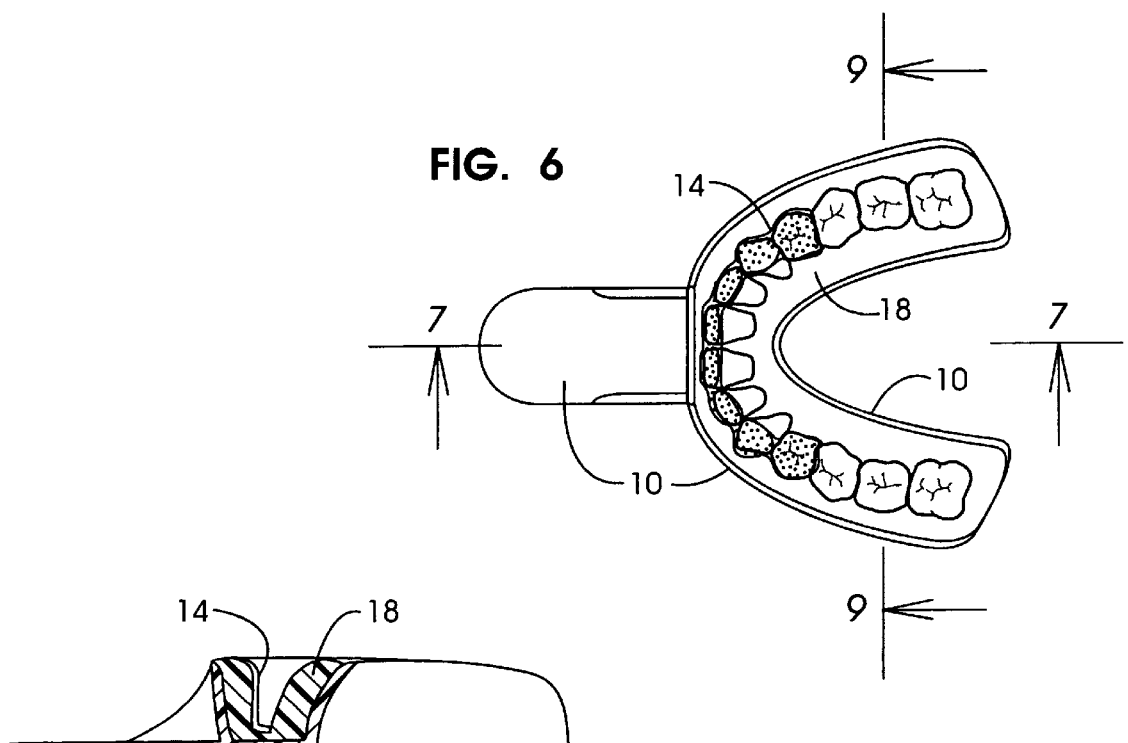
FIG. 6 is a plan view of the completed dental impression prior to wax overlay removal.
Figure 7:
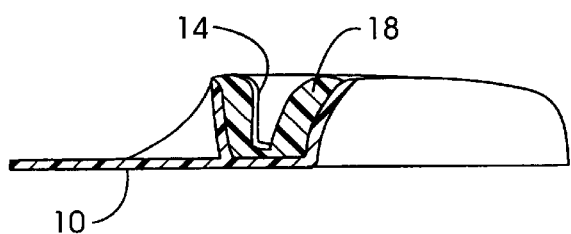
FIG. 7 is a cross-section view taken at line 7—7 of FIG. 6.
Figure 8:
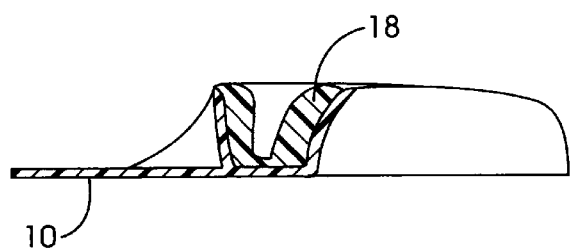
FIG. 8 is a cross-section view similar to FIG. 7 but after accomplishing wax overlay removal.

Following removal of dental impression tray 10 with its included formed patient dental impression 18 from within the patient's mouth, any wax overlay material 14 that is retained on the surfaces of patient dentition impression 18 is manually removed from the impression by appropriate manual scraping or the like. FIGS. 6 and 7 depict the set patient dentition impression 18 with wax overlay material 14 in place. FIG. 8 is similar to FIG. 7 but illustrates the formed patient dental impression 18 with the wax overlay material 14 having been removed.

Next, tray 10 and set patient dentition impression 18 are heated to a temperature of at least about 110° F., preferably in a range of about 110° F. to about 150° F., and more preferably in a range of about 120° F. to about 140° F., by any appropriate means. One exemplary way of accomplishing this, particularly when the dentition impression 18 is made of a material that absorbs radiated microwave energy, as in the case of alginate-base dental impression materials, involves heating the tray and its included patient dental impression in a domestic microwave oven (e.g., a 600 watt input electrical energy rating) at full power for approximately 10 seconds.

Figure 9:
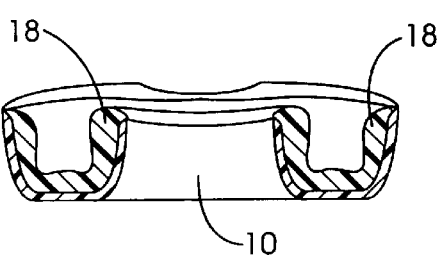
FIG. 9 is a cross-section view taken at line 9—9 of FIG. 6.
Figure 10:
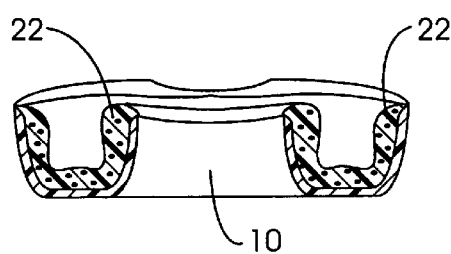
FIG. 10 is a cross-section view taken at line 9—9 of FIG. 8 but with an alternative dental impression material having a particulate filler dispersed therein.

FIG. 9 depicts a dental tray 10 that includes the set patient dentition impression 18, which is formed from an appropriate impression material, e.g., an alginate material. As stated above, either alginate impression materials or other alternative materials such as silicone, polyether or epoxy may include a particulate or fibrous filler. FIG. 10 depicts an impression tray 10 and set patient dentition impression 22 formed from an impression material that includes a particulate filler material. The particulate filler material increases the specific heat of the set patient dentition impression 22 so that it is capable of absorbing and transferring a greater quantity of heat energy per unit of time.

Figure 11:
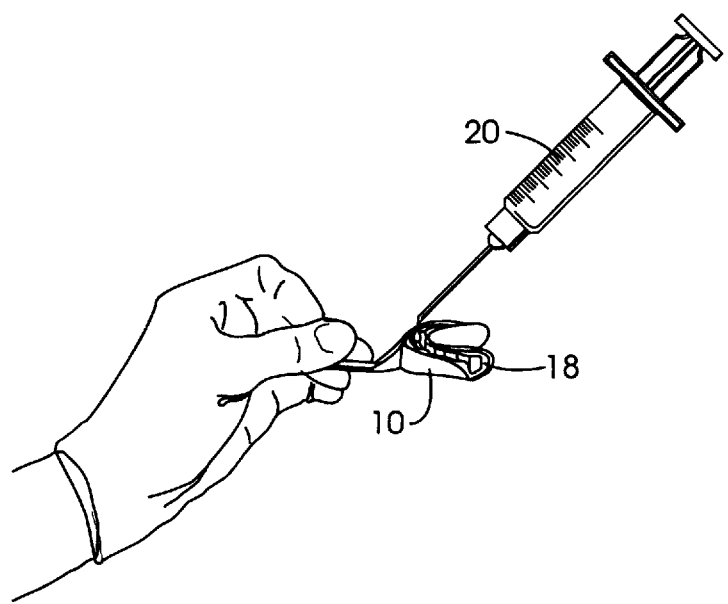
FIG. 11 depicts the step of placing carbamide peroxide or hydrogen peroxide gel into the formed dental impression cavity preparatory to bleaching the patient's teeth.

As shown in FIG. 11, a syringe 20 may be used to place an appropriate dental bleaching composition into the dentition impression 18. An example of an appropriate bleaching composition is a 15% carbamide peroxide gel whitener or bleaching agent, optionally with a fluoride additive. Nevertheless, it should be understood that any bleaching composition known in the art may be used. The surfaces of the set patient dentition impression 18 which correspond to the patient tooth surfaces to be bleached are coated in their labial areas with approximately 0.5 to 1 cc. of the whitening gel. The dental impression tray/patient dental impression is then promptly and properly placed in the patient's mouth (see FIG. 12) and held in place until its temperature falls to below approximately 110° F.

Figure 12:
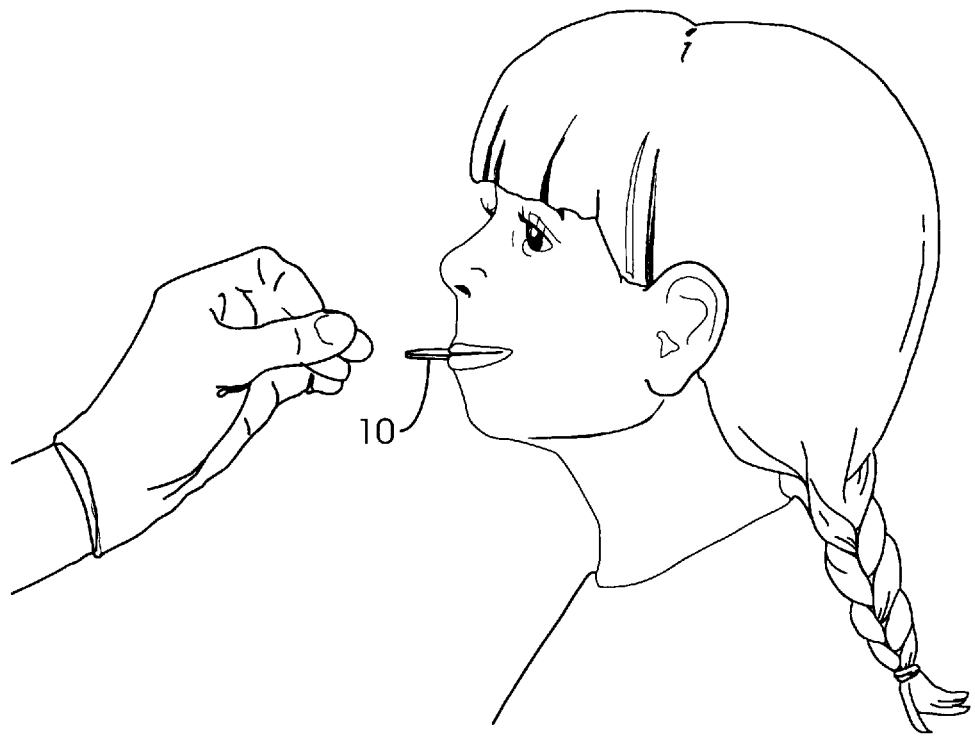
FIG. 12 depicts the placement of the whitening tray of FIG. 11 into the patient's mouth in order to effect bleaching.

Normally the tray is maintained within the patient's mouth at intervals of about 3 to 10 minutes to obtain tooth whitening results that are comparable to those obtained by the prior art practice described above. In order to obtain a satisfactory degree of tooth whitening by the hereinbefore described inventive process, and particularly in the case of non-electrical resistance heating applications, it may be necessary to repeat the steps of heating the dental impression tray impression, inserting additional bleaching composition into the tray, and placing it within the patient's mouth, as illustrated in FIGS. 11 and 12. Thus, the total in-office teeth bleaching or whitening time will generally be in the range of from about 10 minutes to about 20 minutes.

It should be noted that the space filled by the whitening gel following proper tray and patient dental impression insertion into the patient's mouth roughly corresponds to the space or volume occupied by the initially-applied and later-removed dental blocking wax overlay 14. Nevertheless, bleaching will also occur without the use of a blocking overlay 14.

As discussed above with respect to FIG. 10, a modified dental impression material 22 may also be utilized in the practice of the present invention. Unset conventional dental impression material 16 utilized to fill the principal cavity 12 of dental impression tray 10 may be advantageously modified to include, as an additive, a fine, particulate material having a specific heat that is greater than the specific heat of the unmodified dental impression material. As an example, polished, 2 mm.–3 mm. size, stone chips may be added and uniformly mixed into an unset alginate dental impression composition in the ratio of approximately 12-1/2 parts by weight of polished dental stone chips to approximately 87-1/2 parts by weight of unset alginate dental impression material. Inclusion of the aggregate in the composition extends the length of time during which the patient dental impression, following heating by microwave oven equipment, will remain above the minimum temperature of about 110° F. while being held in the patient's mouth.

Figure 13:
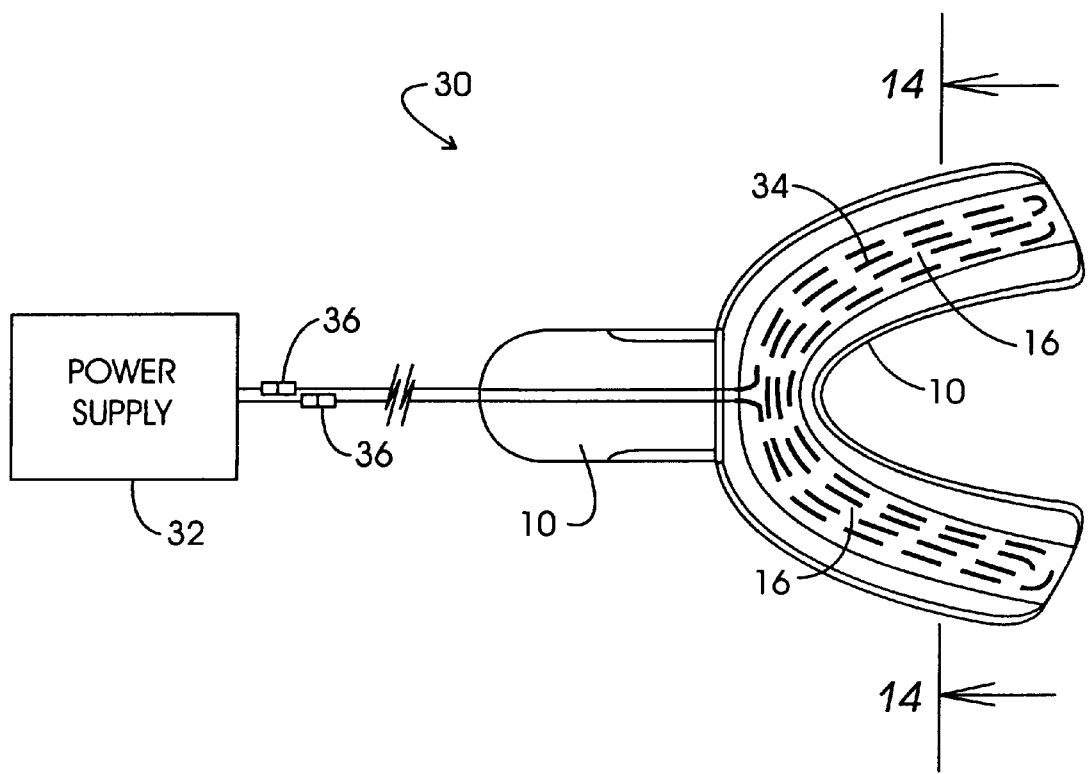
FIG. 13 schematically depicts an alternate embodiment of a dental impression material and impression tray in which resistive heat is employed to heat and maintain the proper temperature of the set dental impression material.
Figure 14:
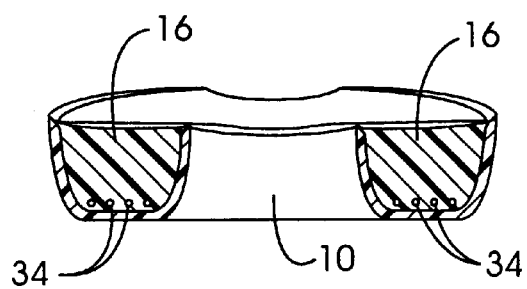
FIG. 14 is a cross-section view taken at line 14—14 of FIG. 13.

FIGS. 13 and 14 pertain to an alternate approach to accomplishing the in-office dental procedure of the present invention for whitening patient teeth utilizing apparatus 30. Such apparatus is basically comprised of a power supply 32 and a looped electrical resistance heating element 34 connected to power supply using conventional electrical disconnects 36. Instead of heating a dental impression tray 10 and its included patient dental impression 18 or 22 in microwave oven equipment, the dental impression tray 10 is provided with looped heating element 34 in the bottom of principal cavity 12 prior to filling the cavity with unset or uncured dental impression material 16. In one application of apparatus 30, approximately 40 to 50 inches of No.24 insulated audio speaker wire were used as resistance heating element 34. Power supply 32 was basically comprised of a conventional 120/30 volt alternating current step-down transformer with a 2.5 ampere output current, an alternating current-to-direct current rectifier, an electronic intermittent switch having 30–40 second on times alternated with 30–40 second off times, and system on-off timer switch mechanism. The power supply timer functioned to activate power supply 32 for periods of time in the range of from 1 to 15 minutes.

Figure 15:
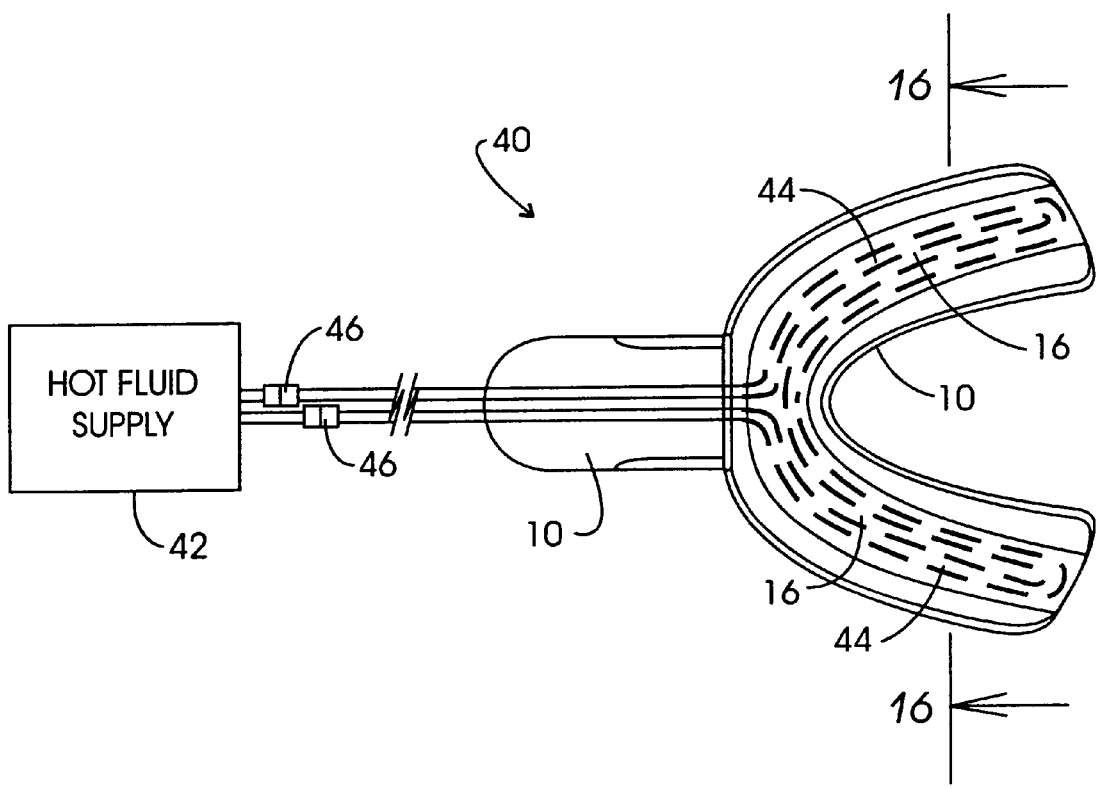
FIG. 15 schematically depicts another alternative embodiment of a dental impression material and impression tray in which a heated fluid is used to heat and maintain the proper temperature of the set dental impression material.
Figure 16:
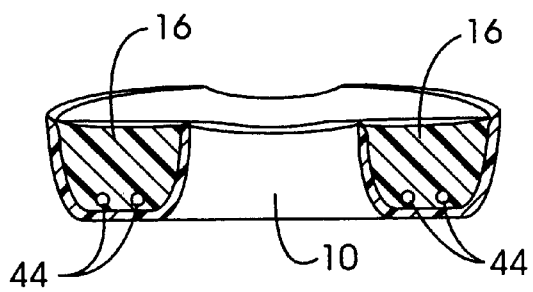
FIG. 16 is a cross-section view taken at line 16-6 of FIG. 15.

FIGS. 15 and 16 pertain to a second alternate approach to accomplish the in-office dental procedure of the present invention for whitening patient teeth utilizing apparatus 40. Such apparatus is basically comprised of a hot fluid supply 42 and a looped tubular fluid conduit 44 connected to hot fluid supply 42 utilizing conventional fluid connectors 46. In this embodiment, the dental impression tray 10 is provided with looped fluid conduit 44 in the bottom of principal cavity 12 prior to filling the cavity with unset or uncured dental impression material 16. In one application of apparatus 40, ⅛ inch rigid plastic fluid conduit was used as fluid conduit 44 connected to a supply 42 of water heated to approximately 130° F. Satisfactory results were obtained where the apparatus was retained in a patient's mouth for a least total period of time in the range of approximately from 5 minutes to 20 minutes.

Utilizing such electrical resistance heating equipment or such fluid heating equipment generally avoids the necessity of repeating steps associated with microwave heating of the dental impression tray. Also, the use of such electrical resistance heating apparatus or such fluid heating equipment is generally necessary in those cases wherein the dental impression material is microwave energy "transparent" as in the case of catalyzed epoxy-based dental impression compounds.

Figure 17:
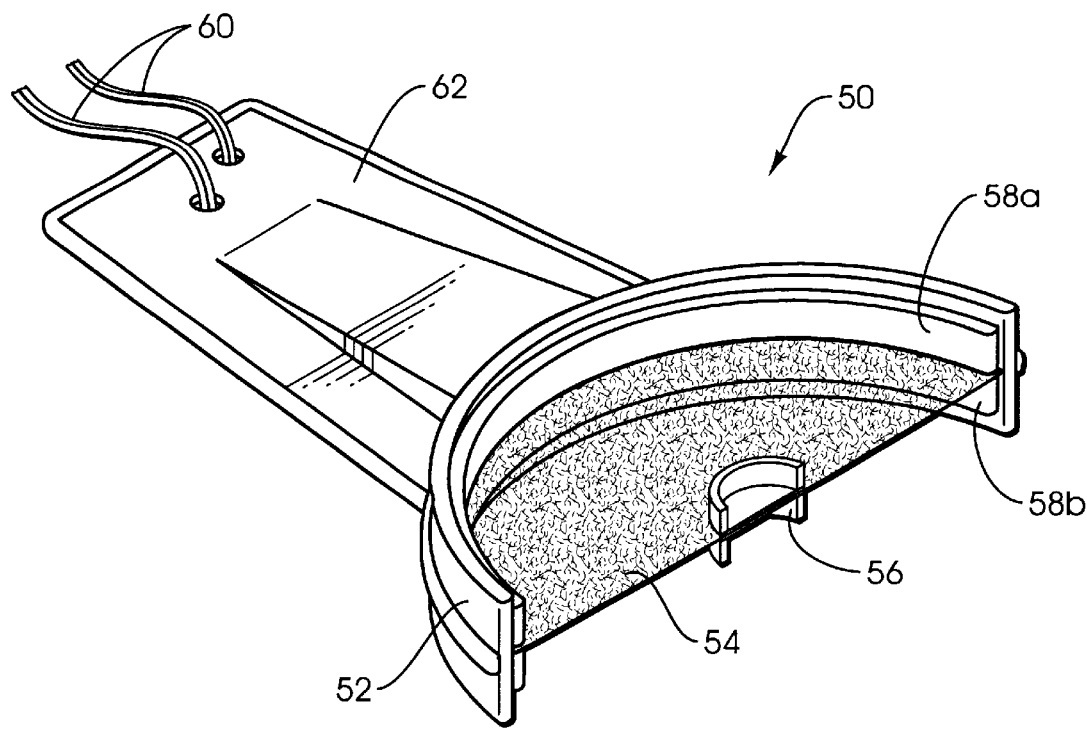
FIG. 17 is a perspective view of an alternative dental impression tray equipped with resistive heating elements.

FIG. 17 depicts an alternative dental impression tray 50 configured so as to be able to treat the upper and lower teeth of a patient of the same time. Dental impression tray 50 includes a generally arcuate structure 52, defining an interior region for receipt of a dental impression material, attached to a handle 62. Handle 62 serves the dual purpose of facilitating gripping by the dentist as well as providing a housing for wires 60 used to heat the dental impression material within dental impression tray 50. Tray 50 further includes a substantially planar divider or barrier 54, which provides opposing surfaces for placing an impression material on either side of divider 54. Divider 54 may comprise any material, for example, a solid metal or plastic sheet, or a wire or nylon mesh. A generally curved wall 56 assists in retaining the alginate or other impression material within the space between arcuate structure 52 and wall 56. FIG. 17 further depicts a pair of heating elements 58a and 58b disposed on an interior surface of arch 52, which are used to heat an impression material.

Figure 18:
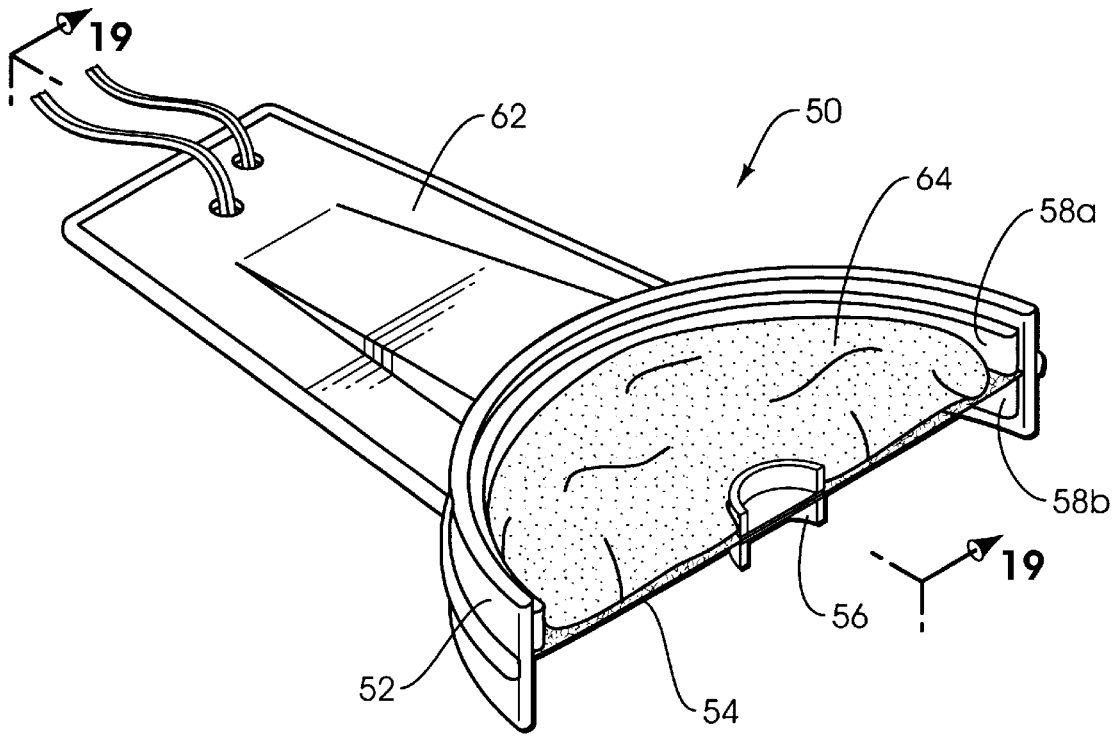
FIG. 18 is a perspective view of the dental impression tray of FIG. 17 into which a dental impression material has been placed into the upper half of the impression tray.

FIG. 18 depicts tray 50 into which an unset impression material 64 has been placed within the space defined by wall 56 and arcuate structure 52 on an upper surface of divider 54. In the case where it will be desired to bleach both the upper and lower teeth a layer of impression material 64 may also be placed on the underside of divider 54. The use of a mesh or other porous material as the divider 54 assists in adhering the impression material 64 onto the surface of divider 54, even on the underside. Of course, glue or other adhesion aids may be used as desired to retain the impression material 64 within the tray 50.

Figure 19:
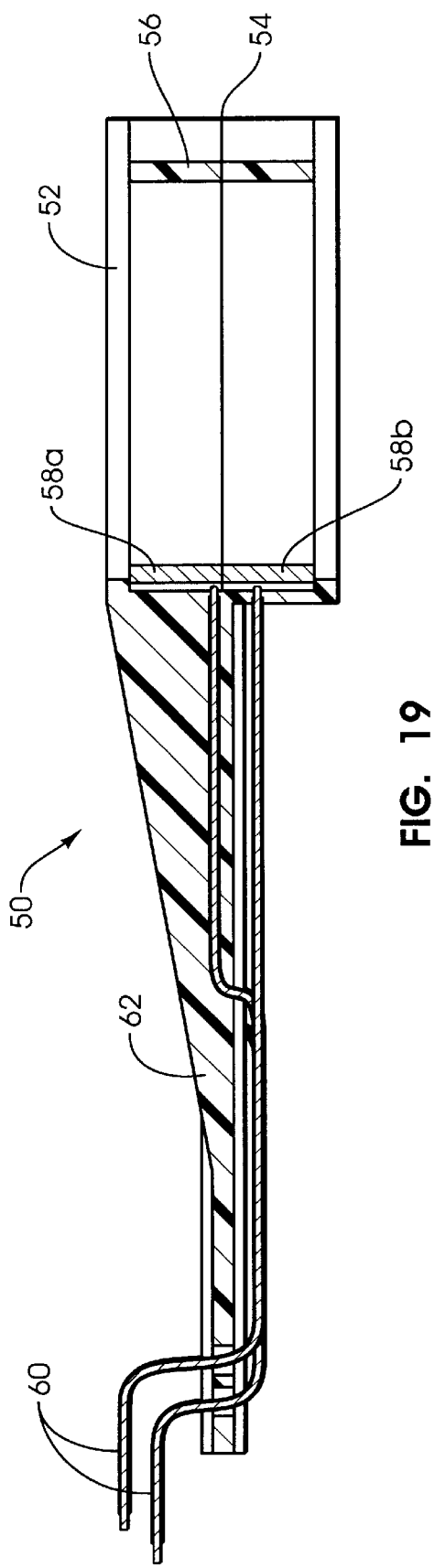
FIG. 19 is a cross-section view taken at line 19—19 of FIG. 18.

Heating elements 58a and 58b heat up as an electrical current is passed therethrough. As shown in FIG. 19, wires 60 deliver an appropriate electrical current to heating elements 58a and 58b. In the alternative, heating elements 58a and 58b may passively act as a heat-sink adjacent to heating element wires (not shown) in contact with elements 58 and 58b. In this way, elements 58a and 58b may not themselves generate heat but act to better disperse heat over a wider area compared to heating element wires in contact with heating elements 58a and 58b.

Figure 20:
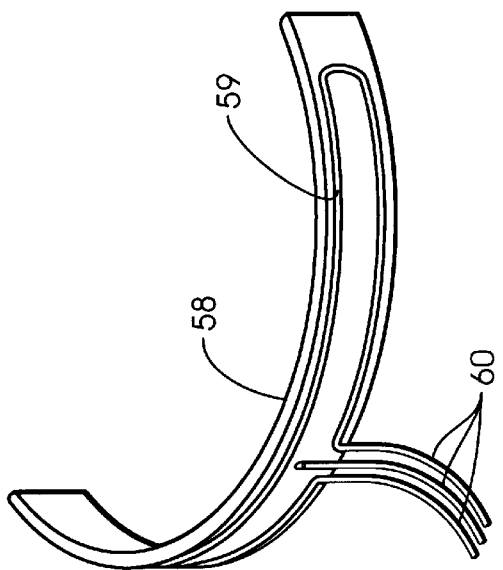
FIG. 20 is a perspective view of a heating element used in a dental impression tray according to the invention.

As more fully depicted in FIG. 20, heating element 58 includes a channel 59 into which wires 60 are placed so as to deliver an appropriate current to the heating element in order to cause heating element 58 to generate heat. In the alternative, wires 60 may include a length of a heating wire, such as a Ni-Cad wire, disposed within channel 59. In this embodiment, the Ni-Cad wire, rather than the metallic heating element 58, will be primarily responsible for generating the heat used to heat up the impression material 64 in order to accelerate bleaching. In this case, metallic heating element 58 will act primarily as a heat sink used to transfer heat energy from the Ni-Cad wire to the impression material 64.

It should be understood that any appropriate energy source may be used so long as it provides a desired quantity of electrical energy in order to heat the impression material to an appropriate temperature. In the embodiment depicted in FIGS. 17 and 20, between 5 and 10 volts of DC current at 1.2 amperes is delivered to each of heating elements 58a and 58b. In order to maximize patient comfort, the patient may be given a temperature control (not shown) so that the patient can increase or lower the power that is delivered to the impression material 64.

In a preferred embodiment, the temperature within the impression material is measured by means of a diode, which is an extremely inexpensive device for measuring temperature and which is preferred where impression tray 50 is intended to be disposable. While diodes are not necessarily as accurate as other devices for measuring temperature, they have adequate accuracy within the narrow temperature ranges involved in the present invention (e.g., about 110–150° F., more preferably about 120–140° F.).

It will be appreciated that a person's gums or gingiva are more sensitive than teeth. Accordingly, it may be desirable to trim back the cured impression material 64 in the area of the gingival interface. In this way, the cured impression material 64 advantageously touches or is adjacent to only the patient's teeth and not the gingiva.

In a preferred treatment regimen, a dental bleaching composition, such as any conventional sticky or non-sticky bleaching composition known in the art, is placed within tray 50 prior to heating. Thereafter, the tray is inserted into the patient's mouth and heated to an appropriate temperature, preferably in a range from about 110° F. to about 150° F., more preferably in a range of about 120° F. to about 140° F. The heated tray is maintained in the patient's mouth for a desired period of time, e.g., from about 1 minute to about 60 minutes, preferably in a range of about 5 to about 30 minutes in order to effect bleaching. It shall be understood, however, that it is certainly within the scope of the invention to preheat the dental tray, either partially or within the desired operating temperature, prior to insertion of the tray into the patient's mouth.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. An apparatus for in-office dental use to whiten a patient's teeth comprising:
   a dental impression tray having a principal cavity;
   an electrical resistance heating element positioned in or adjacent said dental impression tray principal cavity;
   a formed patient dentition impression positioned at least partially within said dental impression tray principal cavity adjacent or embedding said electrical resistance heating element; and
   an electrical power supply removably connected to said electrical resistance heating element, said electrical power supply controllably energizing said electrical resistance element so as to heat and maintain said formed patient dentition impression at a temperature of at least about 110° F. for a period of time of at least about 5 minutes.

2. The apparatus defined by claim 1, wherein the electrical power supply controllably energizes said resistive elements so as to heat and maintain said formed patient dentition impression at a temperature of a range of about 110° F. to about 150° F.

3. The apparatus defined by claim 1, wherein the electrical power supply controllaby energizes said resistive elements so as to heat and maintain said formed patient dentition impression at a temperature of a range of about 120° F. to about 140° F.

4. The apparatus defined by claim 1, wherein the formed patient dentition impression comprises an impression material selected from the group consisting of alginate, silicone, polyether, epoxy, and mixtures of the foregoing, optionally including a filler that increases the heat capacity of the impression material.

5. In a dental office procedure for whitening tooth surfaces of a patient's dentition, a method comprised of using an impression material to form a dentition impression, placing a tooth whitening agent within the dentition impression, placing the dentition impression with the tooth whitening agent contained therein in contact with patient tooth surfaces that are to be whitened, and heating the dentition impression in order to maintain the tooth whitening agent at least about 110° F. for a period of time of at least about 5 minutes.

6. The dental office procedure invention defined by claim 5, wherein said period of time is in a range of approximately 5 minutes to about 60 minutes while maintaining the temperature of the tooth whitening agent within a range of about 120° F. to about 140° F.

7. The dental office procedure invention defined by claim 6, wherein said tooth whitening agent includes at least one of carbamide peroxide or hydrogen peroxide.

8. The dental office procedure invention defined by claim 5, wherein said tooth whitening agent includes at least one of carbamide peroxide or hydrogen peroxide.

9. In a dental office procedure for whitening particular tooth surfaces of a patient's dentition, the steps of:

using an impression material to make a patient dentition impression with included surface areas that register with the patient tooth surfaces that are to be whitened;

applying a tooth whitening agent to said patient dentition impression included surface areas;

inserting said patient dentition impression with applied tooth whitening agent into the patient's mouth with said patient dentition impression included surface areas in registration with the particular patient tooth surfaces that are to be whitened;

heating said patient dentition impression and the applied peroxide tooth-surface bleaching agent and said patient dentition impression to a temperature of at least 110° F.;

inserting said heated patient dentition impression with applied and heated tooth whitening agent into the patient's mouth with said patient dentition impression included surface areas in registration with the particular patient tooth surfaces that are to be whitened; and maintaining said inserted heated patient dentition impression at a temperature of at least about 110° F. within the patient's mouth for a period of time of at least about 5 minutes.

10. The dental office procedure defined by claim 9, wherein the bleaching agent and patient dentition impression are maintained at a temperature in a range of about 120° F. to about 140° F. and in contact with the patient's tooth surfaces to be whitened for a period of time in a range of about 5 minutes to about 60 minutes.

11. The dental office procedure invention defined by claim 9, wherein said tooth whitening agent includes a carbamide peroxide or hydrogen peroxide, and wherein said patient dentition impression includes an alginate.

12. The dental office procedure invention defined by claim 9, wherein said patient dentition impression covers at least a portion of both the patient's upper and lower teeth.

13. In a dental office procedure for whitening particular tooth surfaces of a patient's dentition, a method comprised of:

providing a blocking overlay upon at least a portion of the particular patient tooth surfaces to be whitened;

providing a dental impression tray having a principal cavity;

placing unset dental impression material within said dental impression tray principal cavity;

inserting at least a portion of said dental impression tray with said unset dental impression material into the patient's mouth;

forming a patient dentition impression within said unset dental impression material;

allowing said unset dental impression material within the patient's mouth and in contact with the patient's dentition to cure to thereby form a patient dentition impression with included particular patient tooth surface overlay impressions;

applying a tooth whitening agent to said particular patient tooth surface overlay impressions;

placing said patient dentition impression into the patient's mouth in proper registration with the patient dentition tooth surfaces to be whitened by the tooth whitening agent;

heating said patient dentition impression and tooth whitening agent to a temperature of at least about 110° F.; and maintaining said heated patient dentition impression within the patient's mouth at a temperature of at least about 110° F. for a period of time of at least about 5 minutes.

14. The dental office procedure invention defined by claim 13, wherein said patient dentition impression covers at least a portion of both the patient's upper and lower teeth.

15. The dental office procedure invention defined by claim 14, wherein said tooth whitening agent includes carbamide peroxide or hydrogen peroxide, and wherein said patient dentition impression is an alginate patient dentition impression.

16. The dental office procedure invention defined by claim 13, wherein said heated patient dentition impression is maintained at a temperature in a range of about 120° to about 140° F. and in contact with the patient's tooth surfaces to be whitened for a period of time in a range of about 5 minutes to about 60 minutes.

17. An apparatus for in-office dental use to whiten a patient's teeth comprising:

a dental impression tray having a principal cavity;

a fluid conduit element positioned in said dental impression tray principal cavity;

a formed patient dentition impression positioned in said dental impression tray and embedding said fluid conduit element; and a heated fluid supply removably connected to said fluid conduit element, said heated fluid supply providing heated fluid to said fluid conduit so as to heat said formed patient dentition impression to a temperature of at least about 110° F. for a period of time of at least about 5 minutes.

* * * * *